United States Patent
Zhang et al.

(10) Patent No.: US 10,101,298 B1
(45) Date of Patent: Oct. 16, 2018

(54) PHOTO IONIZATION DETECTOR WITH SELF-CALIBRATION

(71) Applicant: Broadsens Corp., Milpitas, CA (US)

(72) Inventors: Chang Zhang, San Jose, CA (US); Lei Liu, San Ramon, CA (US)

(*) Notice: Subject to any disclaimer, the term of this patent is extended or adjusted under 35 U.S.C. 154(b) by 0 days.

(21) Appl. No.: 15/950,173

(22) Filed: Apr. 11, 2018

Related U.S. Application Data

(60) Provisional application No. 62/486,885, filed on Apr. 18, 2017.

(51) Int. Cl.
*G01N 27/66* (2006.01)
*G01N 33/00* (2006.01)

(52) U.S. Cl.
CPC ......... *G01N 27/66* (2013.01); *G01N 33/0006* (2013.01); *G01N 33/0047* (2013.01)

(58) Field of Classification Search
CPC . G01N 27/66; G01N 33/0006; G01N 33/0047
See application file for complete search history.

(56) References Cited

U.S. PATENT DOCUMENTS

| | | | | |
|---|---|---|---|---|
| 5,010,776 A | * | 4/1991 | Lucero | B09B 1/00 73/863.23 |
| 6,225,633 B1 | * | 5/2001 | Sun | G01N 27/66 250/281 |
| 6,967,485 B1 | * | 11/2005 | Hsueh | G01N 27/64 250/382 |
| 2003/0176804 A1 | * | 9/2003 | Melker | A61B 5/08 600/532 |
| 2011/0056274 A1 | * | 3/2011 | Bunod | G01M 3/229 73/40 |
| 2012/0136268 A1 | * | 5/2012 | Li | G01N 27/66 600/532 |
| 2012/0279277 A1 | * | 11/2012 | Parusel | G01N 27/66 73/1.06 |
| 2014/0091939 A1 | * | 4/2014 | Won | G10K 9/22 340/693.6 |
| 2015/0369784 A1 | * | 12/2015 | Friedrich | G01N 33/0032 436/9 |
| 2016/0266084 A1 | * | 9/2016 | Burge | G01N 33/1826 |

* cited by examiner

*Primary Examiner* — Mark R Gaworecki
(74) *Attorney, Agent, or Firm* — Jigang Jin

(57) ABSTRACT

The present invention discloses a photoionization detector (PID) system that can perform calibrations automatically. The PID system comprises a measurement gas chamber and one or more calibration gas chambers. The one or more calibration gas chambers each hold a type of calibration gas. In one embodiment, a volatile organic compounds (VOCs) measurement and a calibration measurement are conducted in the same gas chamber. In another embodiment, VOCs and calibration measurements are conducted in different gas chambers either simultaneously or at different times.

12 Claims, 3 Drawing Sheets

PHOTO IONIZATION DETECTOR WITH SELF-CALIBRATION

CROSS-REFERENCE TO RELATED APPLICATION

This application claims priority to U.S. provisional patent application Ser. No. 62/486,885, filed Apr. 18, 2017, the entire content of which is incorporated herein by reference.

FIELD OF INVENTION

This invention generally relates to the field of photoionization detection.

BACKGROUND OF THE INVENTION

A photoionization detector (PID) is commonly employed in the detection of volatile organic compounds (VOCs). It utilizes ultraviolet (UV) light to ionize gas molecules and measures electrical signals caused by free electrons and ions. PID systems are highly sensitive and able to detect a wide range of organic compounds and other hazardous chemicals at parts per billion (ppb) levels. PID systems have a relatively long life and do not need frequent replacement. However, since PID systems are sensitive to external factors, e.g., atmospheric pressure and ambient temperature, calibrations are conducted routinely to maintain the measurement accuracy. For instance, after a PID system is moved from one place to another place or the temperature change is beyond a certain range, a calibration is performed. A PID calibration process requires properly trained personnel and a supply of calibration gases. It is time consuming and labor intensive to calibrate a PID system, especially when the system is installed at a location that is difficult to reach (such as above a high ceiling), or dangerous to access (such as inside an underground tank). Therefore, it is desirable to have automated calibrations for a PID system.

SUMMARY OF THE INVENTION

The present invention discloses a PID system that is capable of performing self-calibrations. The system may reduce the labor cost and system down time for VOCs detections significantly. In the present invention, one or more calibration gas chambers are added to a PID system besides a conventional measurement gas chamber. Each calibration gas chamber is filled with a calibration gas, such as isobutylene or clean air, for conducting a calibration measurement. Manual procedures are no longer needed. Automated self-calibrations may be realized.

In one embodiment of the invention, a measurement gas chamber is arranged for not only measuring VOCs but also performing calibration measurements. And one or more calibration gas chambers are used for storage of one or more types of calibration gases, respectively. During a calibration measurement, calibration gas is drawn from a calibration gas chamber and pumped into the measurement gas chamber. Then the calibration gas is ionized and measured. To detect or measure VOCs, air from an external environment is drawn and pumped into the measurement gas chamber. Then, the air is ionized and measured.

In another embodiment of the invention, a measurement gas chamber is used only for measuring VOCs and one or more calibration gas chambers are used for calibration measurements. A gas pumping module is attached to the measurement gas chamber to draw air from an external environment. An opto-mechanical system is arranged to let the gas chambers approach and align with a UV lamp respectively. During a calibration process, one of the calibration gas chambers is aligned with the UV lamp. During measurements of VOCs, the measurement gas chamber is aligned with the UV lamp.

BRIEF DESCRIPTION OF THE DRAWINGS

The subject matter, which is regarded as the invention, is particularly pointed out and distinctly claimed in the claims at the conclusion of the specification. The foregoing and other features and also the advantages of the invention will be apparent from the following detailed description taken in conjunction with the accompanying drawings. Additionally, the leftmost digit of a reference number identifies the drawing in which the reference number first appears.

DETAILED DESCRIPTION

The present invention discloses a PID system that can perform calibrations automatically. The PID system comprises a measurement gas chamber and one or more calibration gas chambers. The one or more calibration gas chambers each hold a type of calibration gas. In one embodiment, VOCs measurements and calibration measurements are conducted in the same gas chamber in different times controlled by one or more gas pumping module. In another embodiment, VOCs and calibration measurements are conducted in different gas chambers, either simultaneously or one at a time.

Figure 1:
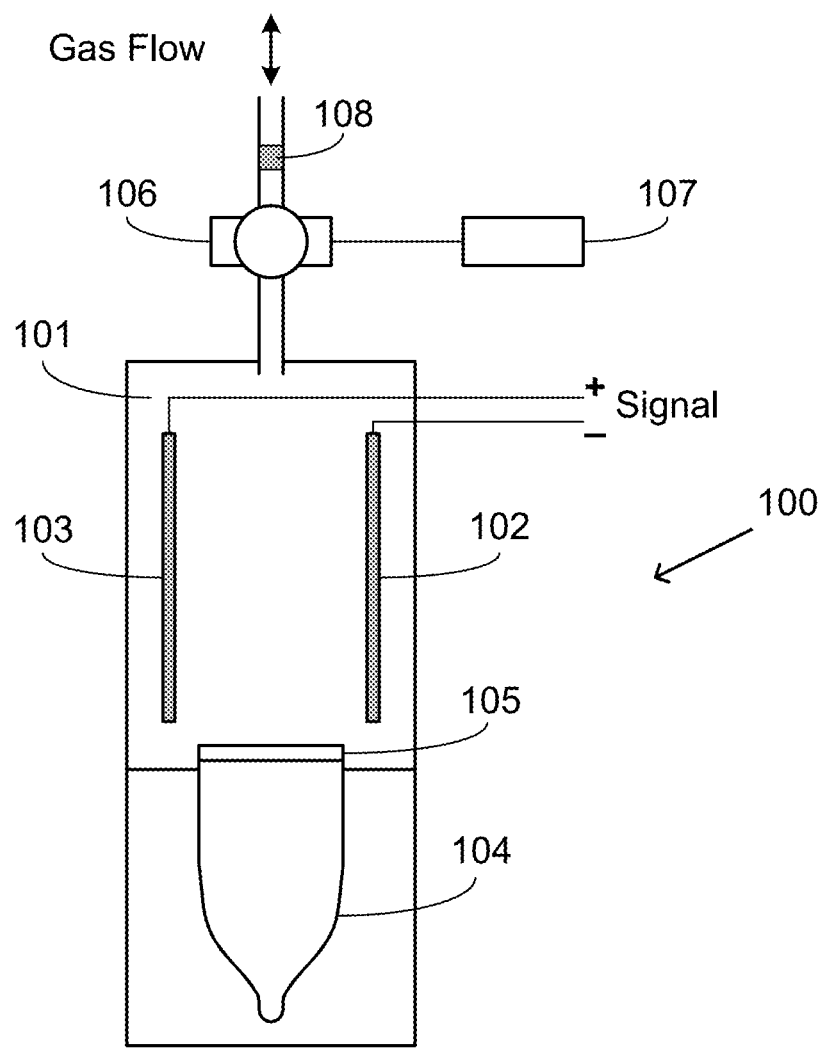
FIG. 1 is a structural diagram of a prior-art PID system.

As shown in FIG. 1, a prior-art PID system 100 has a measurement gas chamber 101, electrodes 102 and 103, a UV lamp 104, a UV lamp window 105, a gas pumping module 106, a controller 107, and a dust filter 108. The gas pumping module 106 is controlled by controller 107. Dust filter 108 is used to remove dust particles from the gas to be tested. The arrow shows directions of gas flow at different times. Before a measurement gets started, the gas pumping module 106 draws gas into gas chamber 101. Then UV lamp 104 is turned on to ionize gas molecules inside the chamber and electrical signals are detected via electrodes 102 and 103. When a measurement of VOCs is performed, air from an external environment is pumped into the gas chamber 101. During a calibration process, a calibration gas is injected into the gas chamber 101. Manual procedures are performed to connect the chamber to a discrete gas cylinder and prevent gas leaks. After the chamber is filled with the calibration gas, UV lamp 104 is turned on. The UV lamp produces an ultraviolet radiation inside gas chamber 101. When gas molecules inside chamber 101 absorb the UV light, they are ionized, which causes ejection of free electrons and the formation of positively charged ions. Some ions and electrons are captured by electrodes 102 and 103. The captured ions and electrons generate an electric signal, which can be detected by a measurement circuit. The greater the gas concentration, the more ions and electrons are generated and the greater the electrical signal. The signals may be amplified by the measurement circuit for further processing.

Inside gas chamber 101, only a small portion of gas molecules is ionized. After the UV lamp is turned off, the ions recapture the free electrons to resume the original state. Therefore, a PID system or measurements of VOCs are non-destructive to gases tested.

Figure 2:
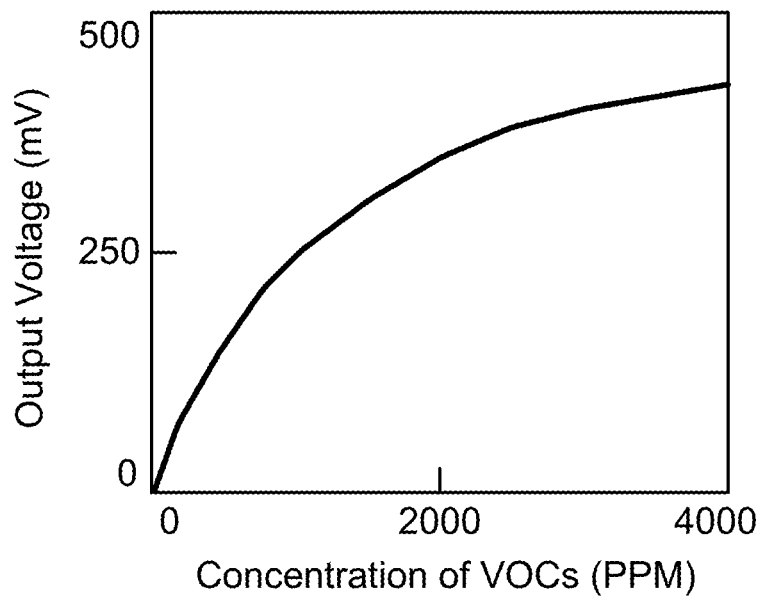
FIG. 2 illustrates a response curve of a PID system.

The relationship between the gas concentration inside a chamber and electrical signals detected is represented by a response curve, as shown schematically in FIG. 2. The curve has a zero voltage reading corresponding to the zero gas concentration, which happens when the chamber is filled with clean air. As the value of concentration increases, so does the output voltage. The curve reflects an ideal case. In reality, the output of a PID system for the same gas concentration may change when the environment changes. For instance, the response curve may shift when the altitude, temperature, or other environmental factors change.

Therefore, a PID system's response curve needs to be calibrated before the first measurement is taken and periodically afterwards. A calibration process typically involves ionizing and measuring the response of one or more known calibration gasses to determine the points of a response curve. Current PID systems require properly trained personnel to fill a chamber with a type of calibration gas and perform a calibration manually. After a calibration process is completed, the calibration gas is discharged. More than one type of calibration gas may be used for better measurement accuracy. Calibration of a PID system typically includes a zero-point calibration and one or more span calibrations. A zero-point calibration determines the zero point of a response curve, i.e., the point where both the output voltage and the gas concentration have a zero reading. The one or more span calibrations determine additional points of a response curve. In practice, clean air is usually used for a zero-point calibration. Some known gases, such as isobutylene, are used as calibration gasses for span calibrations.

In one embodiment of the invention, a measurement gas chamber and one or more calibration gas chambers are included in a PID system. The one or more calibration chambers provide a supply of one or more types of calibration gases, such as isobutylene and clean air. The one or more types of calibration gases are ready to be used anytime without the need of performing any manual procedures. Therefore the PID system can perform a calibration in an automated manner. Due to the non-destructive feature of VOCs measurement, calibration gasses can be reused and thus do not need to be replaced within the life time of a UV lamp.

A PID system measures a sample gas for detections of VOCs. The system also measures one or more types of calibration gasses for calibration purposes. In one embodiment, measurements of VOCs and calibration gases are performed in the same gas chamber at different times. In another embodiment, the measurements are performed at different gas chambers. The embodiments are disclosed in the following sections.

Figure 3:
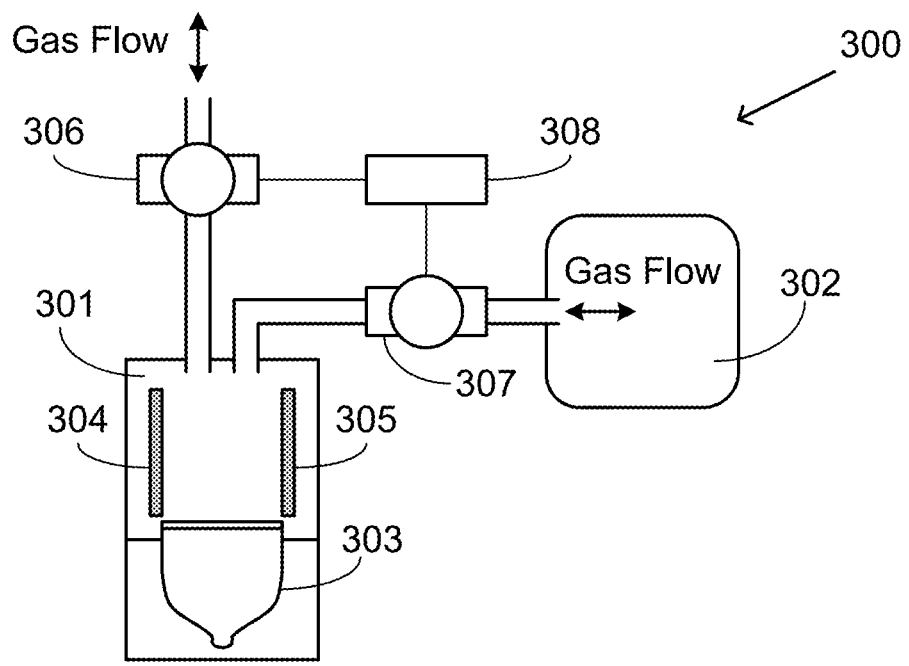
FIG. 3 is a structural diagram of a PID system, according to one embodiment of the present invention.

FIG. 3 is an example of an improved PID system 300 according to one embodiment of the present invention, where all measurements are conducted in the same gas chamber at different times, which is controlled by one or more gas pumping modules. In one embodiment, each gas pumping module may include a pump or fan for drawing gas into a chamber and/or releasing the gas from the chamber and a valve for shutting off the gas flow during measurement operations. Each pump or fan may be bi-directional or at least two pumps or fans are needed if they are unidirectional. System 300 comprises a measurement gas chamber 301, a calibration gas chamber 302, a UV lamp 303, electrodes 304 and 305, gas pumping modules 306 and 307, and a controller 308. The arrows show directions of gas flow at different times. For brevity reasons, a measurement circuit which detects electric signals via the electrodes and details of the gas pumping modules which are commonly used with a gas chamber are not shown in the figure. During a measurement, either a sample air or a calibration gas is drawn into gas chamber 301 via the gas pumping modules 306 or 307. The sample air is taken from an external environment. The calibration gas comes from gas chamber 302 which is used as a storage vessel. Under UV radiations, gas molecules between the electrodes are ionized and then a measurement is conducted for detecting VOCs or calibrating the system. After a calibration measurement is done, the calibration gas is pumped back into calibration gas chamber 302 and stored in the chamber for the next calibration measurement. The calibration gas may be isobutylene or clean air. Again for brevity reasons, only one calibration gas chamber is depicted in the configuration. It is noted that a PID system may have two or more calibration chambers to provide two or more types of reference gases. When clean air is used in a calibration, the zero point of a response curve can be confirmed. When a known gas is used in a calibration, a span point can be identified.

Controller 308 may be configured to regulate the gas pumping modules and to transfer a calibration gas between gas chambers 301 and 302. Thus, no manual procedures are needed for a calibration process.

In another embodiment, measurements are performed at different gas chambers. For instance, calibration gasses are ionized and measured in calibration gas chambers, respectively, and air from an external environment is ionized and measured in a measurement gas chamber. The measurements may be conducted at the same time or different times. Accordingly, there are two designs for this embodiment.

In one implementation, the gasses in a measurement gas chamber and one or more calibration gas chambers are ionized and measured simultaneously. Mirrors and reflectors coated with a semi-reflective film may be used to split UV light from a UV lamp into multiple beams and direct the beams to each gas chamber, respectively. Measurement results from calibration gas chambers are used to calibrate the measurement gas chamber.

Figure 4:
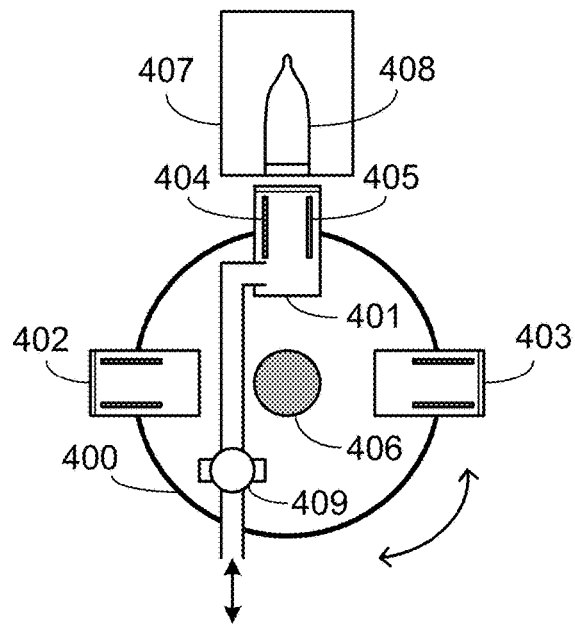
FIG. 4 is another structural diagram of a PID system, according to one embodiment of the present invention.

In another implementation, the gasses in a measurement gas chamber and one or more calibration gas chambers are ionized and measured at different times. Each time, only one chamber is engaged in measuring. FIG. 4 shows an example of such a PID system. There are two main assemblies, a chamber assembly 400 and a radiation source assembly 407. Chamber assembly 400 has three gas chambers 401, 402, and 403, for example. Radiation source assembly 407 has a UV lamp 408. Chamber 401 is a measurement gas chamber for detecting VOCs at a target location. Chamber 401 has two electrodes 404 and 405 and a gas pumping module 409. Air from an external environment may be drawn into chamber 401 by the gas pumping module 409 before measuring. Air in chamber 401 may be discharged by the gas pumping module 409 after a measurement is finished. Again, a measurement circuit and details of the gas pumping modules which are involved in the setup are not shown in the figure for brevity reasons. Chambers 402 and 403 are calibration gas chambers which are arranged for calibration measurements. Calibration gas chambers may hold different types of calibration gases. For instance, gas chambers 402 and 403 may be filled with clean air and isobutylene respectively and their openings are sealed off. The calibration gas chambers each contain two electrodes like electrodes 404 and 405 inside chamber 401. It is noted that a PID system may have more than two calibration chambers for providing more reference gases and calibration measurements.

The three chambers 401, 402, and 403 are positioned along a circular path. A motor 406 is installed at the center of chamber assembly 400. When motor 406 rotates, it causes chamber assembly 400 to rotate along with it. An alignment mechanism or program may be used to drive the motor to rotate the chamber assembly precisely. Each time, rotation of the chamber assembly causes one gas chamber to align with UV lamp 408. Various mature techniques and sensors may be employed to fine tune the alignment. When a calibration measurement is needed, chamber 402 or 403 is rotated to face UV lamp 408. For measurements of air from the external environment, chamber 401 is rotated to face the UV lamp. After a rotation stops and an alignment is completed, an actuator may push assembly 407 forward so that the aligned gas chamber may get closer to UV lamp 408 and expose to stronger UV radiations. Next, the UV lamp 408 may be turned on to irradiate the chamber with UV light and a measurement may begin. Therefore, once again, no manual work is needed. A calibration process may be automated and a PID system may be arranged to perform self-calibration periodically or based on a schedule.

Figure 5:
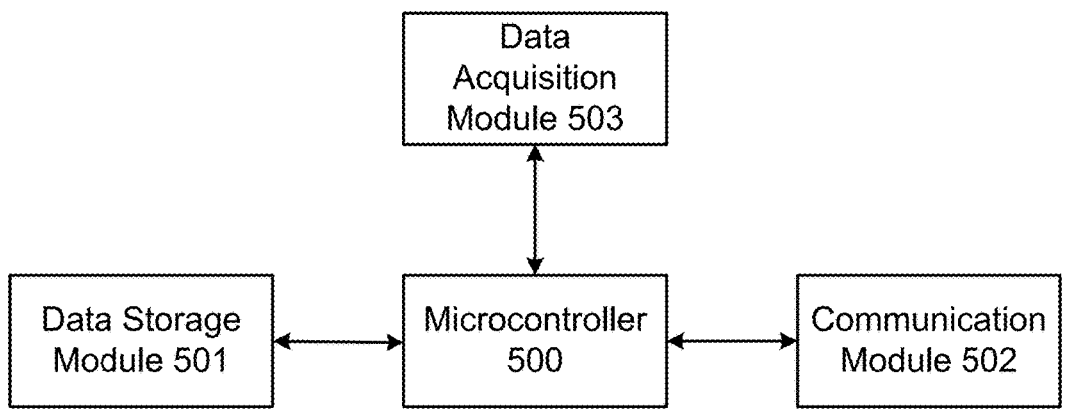
FIG. 5 is a block diagram of a data processing unit of a PID system, according to one embodiment of the present invention.

FIG. 5 is an exemplary block diagram of a control and data processing unit of a PID system. A microcontroller 500 is arranged to control the PID system via a software program. Microcontroller 500 manages a calibration process and adjusts VOCs measurement data using calibration results. A data storage module 501 is used to store calibration data that includes zero point and span points. It also stores measurement results. After a calibration is done, a zero point and span points are updated at storage module 501. A communication module 502 may include a network interface. Via module 502, a user may access the PID system remotely over the network to perform or observe calibrations or scheduled measurements. A data acquisition module 503 is connected to a measurement circuit, which detects and amplifies electrical signals from the electrodes inside a gas chamber. The signals, as measurement data, are sent to microcontroller 500 for further processing.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

We claim:

1. A photoionization detector (PID) system, comprises:
an ultraviolet lamp for providing an ultraviolet radiation;
a measurement gas chamber for measuring volatile organic compounds (VOCs) of a gas from an external environment and performing calibration measurements using one or more types of calibration gases, wherein the calibration measurements are used for calibrating the system;
one or more calibration gas chambers for storing the one or more types of calibration gasses, respectively, wherein the one or more types of calibration gases are transferred to the measurement gas chamber in an automated manner;
a plurality of gas pumping modules, wherein the plurality of gas pumping modules control transferring the one or more types of calibration gases between the measurement chamber and the one or more calibration gas chambers; and
a measurement circuit for receiving electric signals generated by the ultraviolet radiation ionizing one of the one or more types of calibration gas in the measurement gas chamber.

2. The system of claim 1, wherein one of the one or more types of the calibration gases is clean air.

3. The system of claim 1, wherein one of the one or more types of the calibration gases is transferred to the measurement gas chamber from one of the one or more calibration gas chambers for calibration measurement.

4. The system of claim 3, wherein said one of the one or more types of the calibration gases is transferred back to said one of the one or more calibration gas chambers after the calibration measurement is performed.

5. A photoionization detector (PID) system, comprises:
an ultraviolet lamp for providing an ultraviolet radiation;
a measurement gas chamber for performing a target measurement on a gas which comes from an external environment;
one or more calibration gas chambers for performing calibration measurements using one or more types of calibration gasses, wherein the calibration measurements are used for calibrating the system;
a plurality of gas pumping modules; and
a measurement circuit for receiving electric signals generated by the ultraviolet radiation ionizing the gas from the external environment in the measurement gas chamber or one of the one or more types of calibration gases in the one of the one or more calibration gas chambers.

6. The system of claim 5, wherein one of the one or more types of calibration gases is clean air.

7. The system of claim 5, wherein the ultraviolet radiation is split into a plurality of ultraviolet beams.

8. The system of claim 5, wherein the target and calibration measurements are conducted in the measurement gas chamber and the one or more calibration gas chambers simultaneously.

9. The system of claim 5, wherein the target and calibration measurements are conducted at different times.

10. A photoionization detector (PID) system, comprises:
an ultraviolet lamp for providing an ultraviolet radiation;
a measurement gas chamber for performing a measurement on a gas which comes from an external environment;
a plurality of calibration gas chambers for performing multiple calibration measurements using multiple types of calibration gasses, wherein the calibration measurements are used for calibrating the system;
a plurality of gas pumping modules;
a measurement circuit for receiving electric signals generated by the ultraviolet radiation ionizing the gas from the external environment in the measurement gas chamber or one of the one or more types of calibration gases in the one of the one or more calibration gas chambers; and
an alignment mechanism for aligning one of the measurement gas chamber and the plurality of calibration gas chambers with the ultraviolet lamp one at a time.

11. The system of claim 10, wherein one of the one or more types of calibration gases is clean air.

12. The system of claim 10 further including a motor, wherein the motor rotates the measurement gas chamber and the plurality of calibration gas chambers to align with the ultraviolet lamp one at a time.

\* \* \* \* \*